United States Patent [19]

Mori et al.

[11] 4,389,412
[45] Jun. 21, 1983

[54] SUBSTITUTED CYCLOPROPANECARBOXYLIC ACID ESTERS AND PESTICIDAL COMPOSITIONS CONTAINING THE SAME AS ACTIVE INGREDIENT

[75] Inventors: Fumio Mori; Manzo Shiono, both of Kurashiki; Yoshiaki Omura, Okayama Prefecture, all of Japan

[73] Assignee: Kuraray Company, Ltd., Okayama Prefecture, Japan

[21] Appl. No.: 134,589

[22] Filed: Mar. 27, 1980

[30] Foreign Application Priority Data

Mar. 30, 1979 [JP] Japan .................................. 54-39021
Jun. 12, 1979 [JP] Japan .................................. 54-74387

[51] Int. Cl.³ .......................................... A01N 53/00
[52] U.S. Cl. ...................................... 424/305; 560/124
[58] Field of Search ........................... 560/124; 424/305

[56] References Cited

U.S. PATENT DOCUMENTS

| | | | |
|---|---|---|---|
| 3,666,789 | 5/1972 | Itaya | 560/124 |
| 3,927,068 | 12/1975 | Searle | 560/124 |
| 3,973,036 | 8/1976 | Hirano | 560/124 |
| 3,979,424 | 9/1976 | Searle | 560/124 |
| 4,024,163 | 5/1977 | Elliott | 560/124 |
| 4,199,596 | 4/1980 | Fuch . | |

FOREIGN PATENT DOCUMENTS

| | | |
|---|---|---|
| 8331 | 3/1980 | European Pat. Off. . |
| 2805312 | 8/1978 | Fed. Rep. of Germany ...... 560/124 |
| 1243858 | 8/1971 | United Kingdom . |
| 1438129 | 6/1976 | United Kingdom ............... 560/124 |
| 1467579 | 3/1977 | United Kingdom . |

*Primary Examiner*—Michael L. Shippen
*Attorney, Agent, or Firm*—Oblon, Fisher, Spivak, McClelland & Maier

[57] ABSTRACT

A new pyrethroid compound which is low in toxicity to fish and a pesticidal composition containing the same as an active ingredient are provided. The above pyrethroid compound is a substituted cyclopropanecarboxylic acid ester of the general formula:

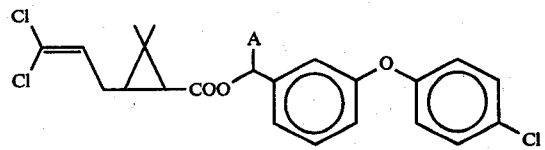

(wherein A is a hydrogen atom or an ethynyl group)

Despite its broad pesticidal spectrum and high pesticidal activity, this ester is very low in toxicity to man and domestic animals and especially low in toxicity to fish as compared with the conventional pyrethroid compounds.

1 Claim, No Drawings

SUBSTITUTED CYCLOPROPANECARBOXYLIC ACID ESTERS AND PESTICIDAL COMPOSITIONS CONTAINING THE SAME AS ACTIVE INGREDIENT

SUMMARY OF THE INVENTION

This invention relates to a substituted cyclopropanecarboxylic acid ester of the following general formula (I) and a pesticidal composition containing the same as an active ingredient.

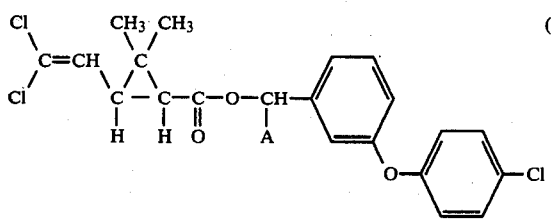

(wherein A is a hydrogen atom or an ethynyl group)

The substituted cyclopropanecarboxylic acid ester of general formula (I) comprises the following two compounds.

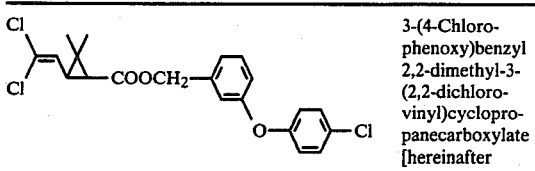

3-(4-Chlorophenoxy)benzyl 2,2-dimethyl-3-(2,2-dichlorovinyl)cyclopropanecarboxylate [hereinafter referred to as Compound (1)]

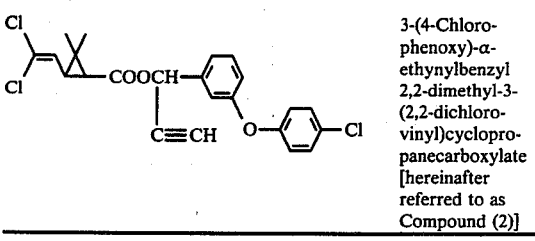

3-(4-Chlorophenoxy)-α-ethynylbenzyl 2,2-dimethyl-3-(2,2-dichlorovinyl)cyclopropanecarboxylate [hereinafter referred to as Compound (2)]

BACKGROUND OF THE INVENTION

Several improved synthetic pyrethroid pesticides have been developed in recent years and, for example, the following synthetic pyrethroid compounds described in the Proceedings of the Tenth Symposium on Agricultural Chemicals (published Sept. 15, 1977), in particular, are now being evaluated for their practical applicability because they have been found to have the advantages mentioned below.

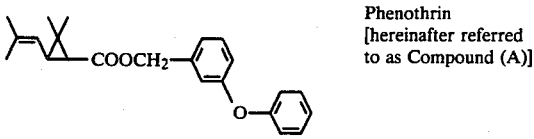

Phenothrin [hereinafter referred to as Compound (A)]

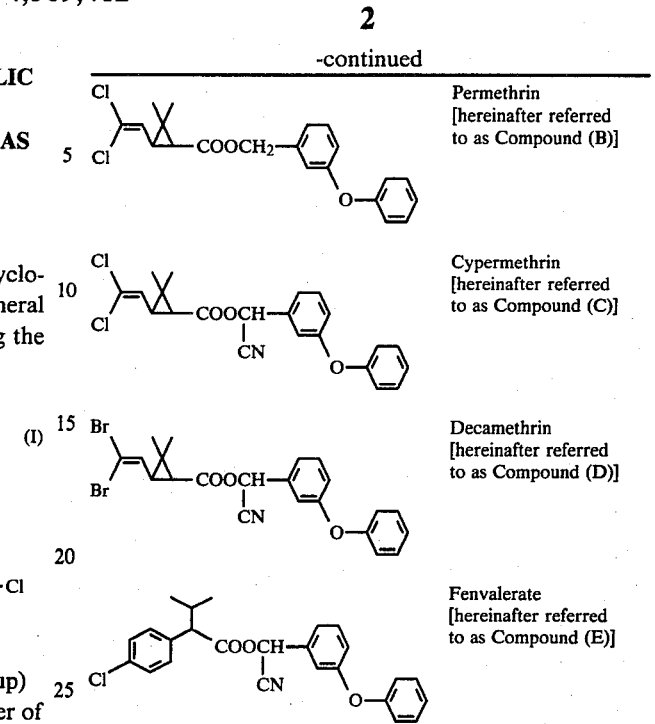

Permethrin [hereinafter referred to as Compound (B)]

Cypermethrin [hereinafter referred to as Compound (C)]

Decamethrin [hereinafter referred to as Compound (D)]

Fenvalerate [hereinafter referred to as Compound (E)]

These compounds are characterized by:
(1) exceptionally high and fast-acting pesticidal effect;
(2) a minimum of environmental residue which is a problem with organochlorine pesticides, whilst they have sufficiently high residual activity;
(3) comparatively low toxicity to man and domestic animals; and
(4) high pesticidal activity even against pests resistant to organophosphorus and/or carbamate pesticides.

Nonetheless, as pointed out in Kagaku-to-Seibutsu (Chemistry and Life) 14, 8 pages 549–556, natural pyrethrin and synthetic pyrethroid pesticides have very high toxicity to fish as compared with the organophosphorus, carbamate or chlorine-type pesticides thus far employed. This means that when such pyrethroid pesticides are applied to a paddy field for the control of agricultural pests, a water area for the control of aquatic pests such as the larvae of mosquitos, sand flies, etc. or a large tract of land including a lake, pond or river, for example by broadcasting from aircraft, these pesticides could destroy the fish inhabiting there. Certain pyrethroid pesticides less toxic to fish were described of late in German Offenlegungsschrift No. 2825197 and it is understood that these compounds represent some improvements in toxicity to fish. However, these pesticides are still by far more toxic to fish than the commonly used organophosphorus, carbamate and chlorine-type pesticides and are not satisfactory for use in the above-mentioned applications.

The intensive study undertaken by the present inventors with a view to developing a safe pesticidal compound which would possess all of the above-mentioned advantages of pyrethroid pesticides, (1) to (4), and, yet, be low in toxicity to fish has revealed that the substituted cyclopropanecarboxylic acid esters of the general formula (I) not only have the above-mentioned advantages (1) to (4) but, to our surprise, have a toxicity to fish which is only 1/5 to 1/1000 of the toxicity of the above pyrethroid pesticides known to have a reduced toxicity to fish and only 1/10 to 1/3000 of the toxicity of the above-mentioned synthetic pyrethroid compounds [i.e. Compounds (A), (B), (C), (D) and (E)]. It was also found that the substituted cyclopropanecarboxylic acid esters of general formula (I) each have a broadened pesticidal spectrum, displaying an unexpectedly high killing effect even on planthoppers to which many of the conventional pyrethroid pesticides are only very sparingly lethal, and do not cause any injury to crop plants. This invention is the culmination of the above findings.

DETAILED DESCRIPTION OF THE INVENTION

The present invention is directed to new pyrethroid compounds which are substituted cyclopropanecarboxylic acid esters of the general formula:

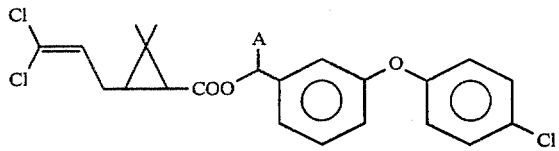

wherein A is a hydrogen atom or an ethynyl group. The subject compounds possess potent, broad spectrum pesticidal activity and are low in toxicity to man, and domestic animals and particularly low in toxicity in fish.

The pesticidal activity of the compounds according to this invention against green rice leafhoppers (*Nephotettix cincticeps* Uhler), rice stem borers (*Chilo suppressalis* Walker), tobacco cutworms (*Prodenia litura* Koch) and houseflies (*Musca domestica*), as examples of the pests against which the same compounds are considered effective, the acute toxicity data on the same compounds as determined in rat by the oral route and the median tolerance limit (TLm) data on the same compounds as determined in killifish (*Orizias latipes*) and guppies (*Lebistes reticulatus*) are shown in Table 1 alongside the corresponding values for various control compounds. The pesticidal effects were determined by the procedures set forth in Test Examples 1 through 4, while the acute toxicity to rat was determined by the procedure set forth in Test Example 9 and the toxicity to fish was determined by the procedures set forth in Test Examples 6 and 7, all those Examples appearing hereinafter.

As will be apparent from Table 1, Test Examples 5 and 8, and Utility Examples 1 and 5 which appear hereinafter, Compounds (1) and (2) according to this invention are at least equivalent or superior in pesticidal effectiveness to control compounds (A), (B), (C), (D), (E), (F), (G) and (H) and, yet, are lower in toxicity to fish than the same control compounds, the toxicity values for our compounds being only one-fifth (1/5) to one-three thousandth (1/3000).

In view of higher pesticidal activity and excellent low toxicity, the Compounds (1) and (2) each consisting principally or essentially of the trans-isomer in relation to the three-membered ring structure are particularly preferable. Compound (2) consisting principally or essentially of the trans-isomer is the most preferable since it is outstanding in pesticidal activity against various pests and is by far low in toxicity to fish, thus being an ideal pesticidal compound which find no equals among pyrethroid compounds which we know of.

TABLE 1

| | Pesticidal Effects | | | | | Toxicity to fish TLm (48 hrs.), ppm | |
|---|---|---|---|---|---|---|---|
| Test compound | Green rice leafhopper (*Nephotettix cincticeps* Uhler) 0.01 μg/Female (%) | Rice stem borer (*Chilo suppressalis* Walker) 1.0 μg/Larva (%) | Tobacco cutworm (*Prodenia litura* Koch) 0.1 μg/Larga (%) | Housefly (*Musca domestica*) 1.0 μg/Female (%) | Acute oral toxicity to rat LD$_{50}$ (mg/kg) | Killifish (*Orizias latipes*) | Guppy (*Lebistes reticulatus*) |
| Compounds of this invention (cis-/trans- = 50:50) | | | | | | | |
| Compound (1) | 100 | 100 | 100 | 100 | >3000 | >10 | >5 |
| Compound (2) | 100 | 100 | 100 | 100 | >3000 | >10 | >10 |
| Control compounds (cis-/trans- = 50:50) | | | | | | | |
| Compound (A) | 80 | 45 | 35 | 100 | — | — | — |
| Compound (B) | 80 | 95 | 85 | 100 | 300 | 0.040 | <0.5 |
| Compound (C) | 100 | 95 | 100 | 100 | 310 | 0.026 | <0.5 |
| Compound (D) | 100 | 100 | 100 | 100 | — | — | <0.5 |
| Compound (E) | 100 | 100 | 100 | 100 | 440 | — | <0.5 |
| | 100 | — | — | 100 | — | — | <0.5 |

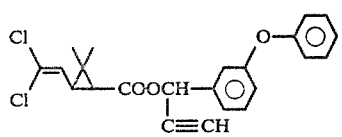

[hereinafter, Compound (F)]

| | 100 | 90 | 65 | 100 | — | 0.15 | <1.0 |

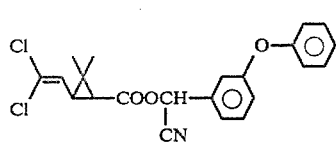

[hereinafter, Compound (G)]

TABLE 1-continued

| | Pesticidal Effects | | | | | Toxicity to fish TLm (48 hrs.), ppm | |
|---|---|---|---|---|---|---|---|
| Test compound | Green rice leafhopper (Nephotettix cincticeps Uhler) 0.01 μg/Female (%) | Rice stem borer (Chilo suppressalis Walker) 1.0 μg/Larva (%) | Tobacco cutworm (Prodenia litura Koch) 0.1 μg/Larga (%) | Housefly (Musca domestica) 1.0 μg/Female (%) | Acute oral toxicity to rat LD$_{50}$ (mg/kg) | Killifish (Orizias latipes) | Guppy (Lebistes reticulatus) |
| Cl₂C=CH−CH(COOCH(CN)−C₆H₄−O−C₆H₄−Br) [hereinafter, Compound (H)] | 100 | 90 | 60 | 100 | — | — | — |

Compounds (1) and (2) according to this invention have excellent pesticidal activity against both the sensitive and resistant strains of pests belonging to the following Orders, displaying a broad pesticidal spectrum. Moreover, the compounds are effective against these pests in all or some of their growth stages.

Order THYSANURA: e.g., *Ctenolepisma villosa Escherich;*

Order COLLEMBOLA: e.g., *Anurida trioculata Kinoshita, Onychiurus pseudarmatus yagii Miyoshi, Sminthurus viridis Linné, Bourletiella hortensis Fitch;*

Order ORTHOPTERA: e.g., Northern cone-headed long horn grasshopper (*Homorocoryphus jezoensis Matsumura et Shiraki*), Vegetable grosshopper (*P. sapporensis Shiraki*), Emma field cricket (*Teleogryllus emma Ohmachi et Matsuura*), Doenitz cricket (*Loxoblemmus doenitzi Stein*), Cockroach (*Blattella germanica Linné*), *Gryllotalpa africana Palisot de Beauvois, Periplaneta fuliginosa Serville;*

Order ISOPTERA: e.g., *Coptotermes formosanus Shiraki;*

Order MALLOPHAGA: e.g., *Menopon gallinae Linné, Damalinia equi Denny, Trichodectes canis De Geer;*

Order ANOPLURA: e.g., *Haematopinus eurysternus Nitzsch;*

Order THYSANOPTERA: e.g., Onion thrips (*Thrips tabaci Lindeman*), *Hercinothrips femoralis Reuter;*

Order HEMIPTERA: e.g., White-backed planthopper (*Sogatella furcifera Horváth*), Brown planthopper (*Nilaparvata lugens Stål*), Small brown planthopper (*Laodelphax striatellus Fallén*), Green rice leafhopper (*Nephotettix cincticeps Uhler*), Zigzag-striped leafhopper (*Inazuma dorsalis Motschulsky*), Black rice bug (*Scotinophara lurida Burmeister*), Rice stink bug (*Lagynotomus elongatus Dallas*), Corbett rice bug (*Leptocorixa corbetti China*), Southern green stink bug (*Nezara viridula Linné*), Grain aphid (*Rhopalosiphum padi Linné*), Japanese grain aphid (*Macrosiphum akebiae Shinji*), Corn leaf aphid (*Rhopalosiphum maidis Fitch*), Green peach aphid (*Myzus persicae Sulzer*), Cotton aphid (*Aphis gossypii Glover*), Foxglove aphid (*Aulacorthum solani Kaltenbach*), Soy bean aphid (*Aphis glycines Matsumura*), Small bean bug (*Chauliops fallax Scott*), Bean bug (*Riptortus clavatus Thunberg*), Common green stink bug (*Nezara antennata Scott*), Unibanded stink bug (*Piezodorus rubrofasciatus Fabricius*), Sloe bug (*Dolycoris baccarum Linné*), Oriental chinch bug (*Cavelerius saccharivorus Okajima*), Sugarcane cottony aphid (*Ceratovacuna lanigera Zehntner*), Cabbage aphid (*Brevicoryne brassicae Linné*), Small green plant bug (*Lygus lucorum Meyer-Dur*), Onion aphid (*Neotoxoptera formosana Takahashi*), Arrowhead scale (*Unaspis yanonensis Kuwana*), California red scale (*Aonidiella aurantii Maskell*), *Viteus vitifolii Fitch*, Grape leafhopper (*Erythroneura apicalis Nawa*), Grape whitefly (*Aleurolobus taonabae Kuwana*), Ume globose scale (*Eulecanium kunoense Kuwana*), Chrysanthemum aphid (*Macrosiphoniella sanborni Gillette*), Rose aphid (*Macrosiphum ibarae Matsumura*), Azalea lacewing bug (*Stephanitis pyrioides Scott*), Fern scale (*Pinnaspis aspidistrae Signoret*);

Order TRICHOPTERA: e.g., *Oecetis nigropunctata Ulmer;*

Order DIPTERA: e.g., Rice steam maggot (*Chlorops oryzae Matsumura*), Rice leaf miner (*Agromyza oryzae Munakata*), Small rice leaf miner (*Hydrellia griseola Fallén*), Paddy steam maggot (*Hydrellia sasakii Yuasa et Ishitani*), Wheat thigh chloropid fly (*Meromyza saltatrix Linne*), Leaf miner, Wheat blossom midge (*Sitodiplosis mosellana Gehin*), Soy bean root miner (*Melanagromyza dolichostigma DE Meijere*), Soy bean steam midge (*Profeltiella soya Monzen*), Soy bean stem miner (*Melanagromyza sojae Zehntner*), Soy bean pod gall midge (*Aspondylia sp.*), Seed maggot (*Hylemya platura Meigen*), Onion maggot (*Hylemya antiqua Meigen*), Stone leek leaf miner (*Phytobia cepae Hering*), Narcissus bulb fly (*Lampetia equestris Fabricius*), House fly (*Musca domestica vicina*), Mosquito (*Culex pipiens*);

Order APHANIPTERA: e.g., *Xenopsylla cheopis Rothschild, Pulex irritans Linne;*

Order HYMENOPTERA: e.g., *Dolerus hordei Rohwer*, Soy bean sawfly (*Takeuchiella pentagona Malaise*);

Order LEPIDOPTERA: e.g., Rice stem borer (*Chilo suppressalis Walker*), Yellow rice borer (*Tryporyza incertulas Walker*), Pink borer (*Sesamia inferens Walker*), *Pelopidas mathias oberthuri Evans*, Grass leaf roller (*Cnaphalocrocis medinalis Guénée*), Rice leaf roller (*Susumia exigua Butler*), Rice green caterpillar (*Naranga aenescens Moore*), Armyworm (*Leucania separata Walker*), Corn borer (*Ostrinia furvacalis Guénée*), Sweetpotato leaf folder (*Brachmia triannulella Herrich-Schaaffer*), Bindweed leaf miner (*Bedellia sommulentella Zeller*), Sweetpotato leaf worm (*Aedia leucomelas Linné*), Flax budworm (*Heliothis viriplaca adaucta Butler*), Tabacco striped caterpillar (*Pyrrhia umbra Hufnagel*), Bean webworm (*Syllepte ruralis Scopli*), Soy bean pod borer (*Grapholitha glycinivorella Matsumura*), Azuki pod worm (*Matsumuraeses phaseoli Matsumura*), Lima-bean pod borer (*Etiellazinckenella Treitschke*), Oriental tobacco budworm (*Helicoverpa assulta* Guenée), Peppermint pyrausta (*Pyrausta aurata* Scopoli), Peacock butterfly, Lilac pyralid (*Margaronia nigropunctalis* Bremer), Sugarcane shoot borer (*Eucosma schistaceana* Snellen), Cabbage armyworm (*Mamestra brassicae* Linné), Tobacco cutworm (*Plodenia litura* Fabricius), Common cutworm (*Agrotis fucosa* Butler), Common cabbageworm (*Pieris rapae crucivora* Boisduval), Crucifer caterpillar (*Mesographe forficalis* Linné), Diamondback moth (*Plutella maculipennis* Curtis), Cotton caterpillar (*Margaronia indica* Saunders), Stone leek miner (*Acrolepia alliella* Semenov et Kuznetsov), Citrus leaf miner (*Phyllocnistis citrella* Stainton), Smaller citrus dog (*Papilio xuthus* Linné), Peach fruit moth (*Carposina niponensis* Walsingham), Oriental fruit moth (*Grapholitha molesta* Busck), Summer fruit tortrix (*Adoxophyes orana* Fischer von Roslerstamm), Gypsy moth (*Lymantria dispar* Linne), Tent caterpillar (*Malacosoma neustria testacea* Motschulsky), Small grape plume moth (*Stenoptilia vitis* Sasaki), Persimmon fruit moth (*Stathmopoda flavofasciata* Nagano), Fall webworm (*Hyphantria cunea* Drury), Japanese lawn grass cutworm (*Rusidrina depravata* Butler), Pectinophora gossypiella;

Order COLEOPTERA: e.g., Rice leaf beetle (*Oulema oryzae* Kuwayama), Large 28-spotted lady beetle (*Henosepilachna vigintioctomaculata* Motschulsky), 28-spotted lady beetle (*H. vigintioctopunctata* Fabricius), False melon beetle (*Atrachya menetriesi* Faldermann), Two-striped leaf beetle (*Paraluperodes nigrobilineatus* Motschulsky), Bean leaf beetle (*Colposcelis signata* Motschulky), Bean frosted weevil (*Eugnathus distinctus* Roelofs), Castaneous garden beetle (*Maladera castanea* Arrow), Soy bean beetle (*Anomala rufocuprea* Motschulsky), Bean blister beetle (*Epicauta gorhami* Marseul), Peppermint leaf beetle (*Chrysolina exanthematica* Wiedemann), Olive engraved weevil (*Hylobius cribripennis* Matsumura et Kono), Vegetable weevil (*Listroderes obliquus* Klug), Cucurbit leaf beetle (*Aulacophora femoralis* Motschulsky), Boll weevil (*Anthonomus grandis* Boh.), Rice weevil (*Sitophilus zeamais* Motschulsky), Lesser grain borer (*Rhizopertha dominica* Fabricius), Azuki bean weevil (*Callosobruchus chinensis* Linné), Mustard beetle (*Phaedon cochleariae* Fab.), Boll weevil;

Order ACARINA: e.g., Winter grain mite (*Penthaleus major* Dugès), Two-spotted spider mite (*Tetranychus urticae* Koch), Carmine mite (*Tetranychus telarius* Linné); and so forth.

The substituted cyclopropanecarboxylic acid esters of general formula (I) can be easily produced, for example by the following method.

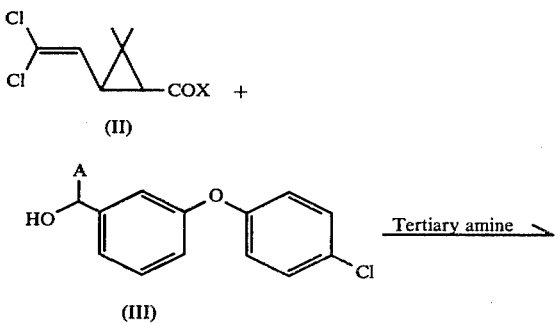

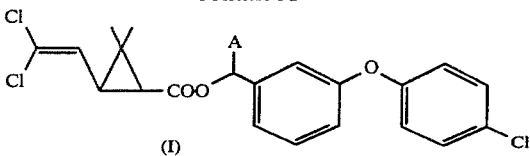

[wherein A has the same meaning as defined in general formula (I); and X is a halogen atom]

Thus, the above process is carried out by reacting a 2,2-dimethyl-3-(2,2-dichlorovinyl)cyclopropanecarbonyl halide of general formula (II) with a substituted benzyl alcohol of general formula (III) in the presence of a tertiary amine such as pyridine, triethylamine or the like.

In putting to use the compounds according to this invention, each of them or a mixture thereof may be employed as it is. However, for the sake of ease of handling, it is generally an acceptable practice to formulate the compounds with suitable carriers or vehicles to prepare stock preparations and, then, dilute them as required. The applicable formulations include, for example, emulsifiable concentrates, wettable powders, dusts, granules, microgranules, oil preparations, aerosols, thermal fumigants (fumigation coils, electric fumigation mats or other formed articles), non-thermal fumigants, baits, etc. These and other optional formulations may be prepared by the established manufacturing procedures for agricultural chemicals and may be selectively applied according to the intended use.

Unlike the conventional chrysanthemummonocarboxylates, the compounds according to this invention are highly stable against light, heat, oxidation, etc. However, if it is considered necessary, for example when exposure to a highly oxidative environment is expected, compositions with stabilized efficacy can be prepared by incorporating suitable amounts of oxidation inhibitors or ultraviolet absorbers such as phenol derivatives, e.g. BHT, BHA, etc., bisphenol derivatives, arylamines such as phenyl-α-naphthylamine, phenyl-β-naphthylamine, phenetidine-acetone condensate, etc. or/and benzophenone compounds as stabilizers.

Generally such a pesticidal composition contains 0.01 to 95 weight percent, preferably 0.1 to 90 weight percent, of the compound according to this invention.

The compounds according to this invention can be used in the above-mentioned various formulations and in various application forms obtainable by processing the formulations further to suit the purpose. In such secondary application forms, the content of the compound according to this invention may vary in a very wide range. Thus the concentration of said compound in an application form is 0.0000001 to 100 weight percent, preferably 0.0001 to 10 weight percent.

The pesticidal compositions according to this invention can be applied by the conventional application method or methods suited for each application form.

The following Examples of Synthesis, Test Examples, Formulation Examples and Utility Examples are intended to further illustrate this invention and should by no means be construed as limiting the scope of the invention. In the Formulation Examples, all parts are by weight.

EXAMPLE OF SYNTHESIS-1

In 20 ml of dry benzene was dissolved 2.28 g of cis-2,2-dimethyl-3-(2,2-dichlorovinyl)cyclopropanecarbonyl chloride, followed by addition of 2.34 g of 3-(4-chlorophenoxy)benzyl alcohol and 1.58 g of pyridine. The mixture was stirred at room temperature overnight. Thereafter, the reaction mixture was washed with dilute hydrochloric acid and water, dried over anhydrous magnesium sulfate and distilled under reduced pressure to remove a low-boiling fraction, whereby an oily product was obtained as a residue. This oil was purified by preparative liquid chromatography [column: Waters Associates' Prep LC/System 500, Prep PAK® 500/SILICA; solvent system: diisopropyl ether:n-hexane=6:94, v/v]. The above procedure yielded 3.91 g of 3-(4-chlorophenoxy)benzyl cis-2,2-dimethyl-3-(2,2-dichlorovinyl)cyclopropanecarboxylate (yield 92%).

The above procedure was repeated except that trans-2,2-dimethyl-3-(2,2-dichlorovinyl)cyclopropanecarbonyl chloride was used in lieu of cis-2,2-dimethyl-3-(2,2-dichlorovinyl)cyclopropanecarbonyl chloride. This procedure yielded 3.81 g of 3-(4-chlorophenoxy)benzyl trans-2,2-dimethyl-3-(2,2-dichlorovinyl)cyclopropanecarboxylate (yield 90%).

The above product compounds have the following NMR spectra.

NMR spectra (90 MHz) $\delta_{HMS}^{CDCl_3}$:

cis-Compound: 1.17(s)6H, 1.72–2.08(m)2H, 5.00(s)2H, 6.18(d)1H, 6.80–7.38(m)8H trans-Compound: 1.11(s)3H, 1.21(s)3H, 1.56(d)1H, 2.18(dd)1H, 5.03(s)2H, 5.53(d)1H, 6.80–7.38(m)8H

EXAMPLE OF SYNTHESIS-2

In 120 ml of dry benzene was dissolved 11.4 g of 2,2-dimethyl-3-(2,2-dichlorovinyl)cyclopropanecarbonyl chloride (cis-/trans-ratio=50:50, approx.) followed by addition of 12.9 g. of 3-(4-chlorophenoxy)-α-ethynylbenzyl alcohol and further by dropwise addition of 7.9 g of pyridine. The mixture was stirred at room temperature overnight. Thereafter, the reaction mixture was diluted with 100 g of water and the benzene layer was separated, washed with dilute hydrochloric acid and water and dried over anhydrous magnesium sulfate. The low-boiling fraction was then distilled off under reduced pressure to recover an oil. This oily product was purified by preparative liquid chromatograpy [column: Water's Associates' Prep LC/System 500, Prep PAK® 500/SILICA; solvent system: diethyl ether:n-hexane=2:98]. The above procedure yielded 20.2 g of 3-(4-chlorophenoxy)-α-ethynylbenzyl 2,2-dimethyl-3-(2,2-dichlorovinyl)cyclopropanecarboxylate (yield 90%). The separation of cis- and trans-isomers from each other can be effected by the above-mentioned preparative liquid chromatography. The NMR spectra of such isomers are indicated below.

NMR spectra (90 MHz) $\delta_{HMS}^{CDCl_3}$:

cis-Compound: 1.13, 1.16, 1.20, 1.23(each s)6H; 1.72–2.10(m)2H; 2.53–2.60(m)1H; 6.16(d), 6.18(d)1H; 6.32–6.40(m)1H; 6.75–7.43(m)8H trans-Compound: 1.08, 1.13, 1.17, 1.25(each s)6H; 1.56(d), 1.58(d)1H; 2.04–2.31(m)1H; 2.52–2.61(m)1H; 5.55(d)1H; 6.36–6.43(m)1H; 6.76–7.43(m)8H

EXAMPLE OF SYNTHESIS-3

The procedure followed in Example of Synthesis-2 was repeated except that 11.7 g of 3-(4-chlorophenoxy)benzyl alcohol was used in lieu of 12.9 g. of 3-(4-chlorophenoxy)-α-ethynylbenzyl alcohol. The resultant oily product was purified by preparative liquid chromatography to obtain 19.6 g of 3-(4-chlorophenoxy)benzyl 2,2-dimethyl-3-(2,2-dichlorovinyl)cyclopropanecarboxylate (yield 92%). The NMR spectra of the cis- and trans-isomers obtained by preparative liquid chromatography are in agreement with the spectra of the compounds according to Example of Synthesis-1.

TEST EXAMPLE-1

Mortality test with houseflies (*Musca domestica*) by topical application method Each of the compounds according to this invention and the control compounds (Table 2) was accurately weighted and a 0.1% solution of each sample in acetone was prepared. Female adult houseflies (*Musca domestica*) resistant to organophosphorus pesticides, were anesthetized with ether and 0.5 μl or 1.0 μl of the above solution was micropipetted onto the prothoracic dorsal region of each insect. The insects were then put in a high-walled dish together with feed and the dish was covered with a wire-mesh cover and kept at a temperature of 25° C. The test insects were used in groups of 30 individuals each. After 24 hours the insects were examined for deaths and the percent mortality was calculated. The results are set forth in Table 2.

TABLE 2

| Test compound | | % Mortality | |
| --- | --- | --- | --- |
| | | 0.5 μg/Female | 1.0 μg/Female |
| Compound (1) | cis- | 100 | 100 |
| | trans- | 100 | 100 |
| | cis-/trans- = 50:50 | 100 | 100 |
| Compound (2) | cis- | 100 | 100 |
| | trans- | 100 | 100 |
| | cis-/trans- = 50:50 | 100 | 100 |
| Compound (A) | " | 97 | 100 |
| Compound (B) | " | 100 | 100 |
| Compound (C) | " | 100 | 100 |
| Compound (D) | " | 100 | 100 |
| Compound (E) | — | 100 | 100 |
| Compound (F) | cis-/trans- = 50:50 | 100 | 100 |
| Compound (G) | " | 100 | 100 |
| Compound (H) | " | 100 | 100 |
| 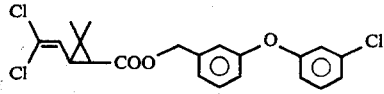 | " | 60 | 93 |

TABLE 2-continued

| Test compound | | % Mortality | |
|---|---|---|---|
| | | 0.5 μg/Female | 1.0 μg/Female |
| 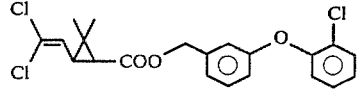 | " | 30 | 60 |
| 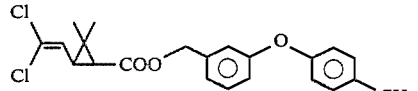 | " | 80 | 100 |
| 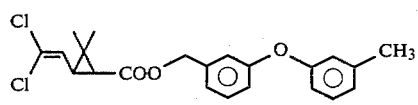 | " | 50 | 80 |
| 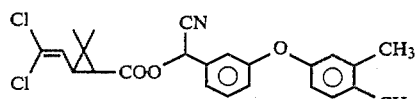 | " | 40 | 80 |
| 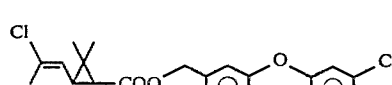 | " | 0 | 20 |
| 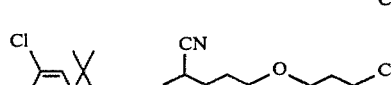 | " | 0 | 27 |

TEST EXAMPLE-2

Mortality test with green rice leafhoppers (*Nephotettix cincticeps* Uhler) by topical application method Each of the compounds according to this invention and the control compounds (Table 3) was accurately weighed and dissolved in acetone to prepare a solution of predetermined concentration. Female adult green rice leafhoppers (*Nephotettix cincticeps* Uhler) resistant to organophosphorus and carbamate pesticides were anesthetized with carbon dioxide gas and 0.5 μl of the above solution was micropipetted onto the thoracic abdominal region of each insect. Then, the insects were kept at 25° C. with access to rice plant seedlings. The insects were used in groups of 15 individuals each. After 24 hours, the insects were examined for deaths and the percent mortality was calculated. The results are shown in Table 3.

TABLE 3

| Test compound | | % Mortality | | |
|---|---|---|---|---|
| | | 0.01 μg/Female | 0.1 μg/Female | 1.0 μg/Female |
| Compound (1) | trans- | 100 | 100 | 100 |
| | cis-/trans- = 50:50 | 100 | 100 | 100 |
| Compound (2) | cis- | 100 | 100 | 100 |
| | trans- | 100 | 100 | 100 |
| | cis-/trans- = 50:50 | 100 | 100 | 100 |
| Compound (A) | " | 80 | 100 | 100 |
| Compound (B) | " | 80 | 100 | 100 |
| Compound (C) | " | 100 | 100 | 100 |
| Compound (D) | " | 100 | 100 | 100 |
| Compound (E) | — | 100 | 100 | 100 |
| Compound (F) | cis-/trans- = 50:50 | 100 | 100 | 100 |
| Compound (G) | " | 100 | 100 | 100 |
| Compound (H) | " | 100 | 100 | 100 |
| 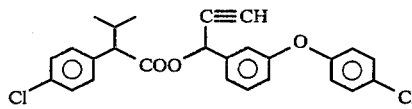 | | 33 | 100 | 100 |

[hereinafter referred to as Compound (K)]

Furthermore, there was determined by the above method the median lethal dose [LD$_{50}$: the amount of each test compound which killed 50% of dosed green TABLE 7-continued

| Test compound | | Percent decrease of population (%) |
|---|---|---|
| | trans- | 100 |
| | cis-/trans- = 50:50 | 100 |
| Compound (B) | cis-/trans- = 50:50 | 100 |

TEST EXAMPLE-6

Fish toxicity test with killifish (*Orizias latipes*)

An acetone solution of one of the test compounds as mentioned in Table 8 was prepared by adding said test compound to 15 ml of acetone. To 10 liters of water was added a predetermined amount of the above acetone solution and the mixture was stirred thoroughly to prepare an aqueous solution containing the test compound in a predetermined concentration. This was used as a test water. After the each test water was moderately aerated, ten killifishes (*Orizias latipes*) with a body weight of about 0.25 g and a body length of about 2.5 cm were released into said each test water which was maintained at 25±1° C. After 48 hours, the test fish was examined for death. The TLm (median tolerance limit, ppm) was determined. The results are set forth in Table 8.

TABLE 8

| Test compound | | TLm (48 hrs.) ppm |
|---|---|---|
| Compound (1) | cis- | >10 |
| | trans- | >10 |
| | cis-/trans- = 50:50 | >10 |
| Compound (2) | cis- | >10 |
| | trans- | >10 |
| | cis-/trans- = 50:50 | >10 |
| Compound (B) | " | 0.040 |
| Compound (C) | " | 0.026 |
| Compound (G) | " | 0.15 |

TEST EXAMPLE-7

Fish toxicity test with guppies (*Lebistes reticulatus*)

To 5 liters of water were added 250 mg of Sorpol SM-200 (trademark, Toho Chemical Co., Ltd.) as a surfactant and 2.5 ml of an acetone solution containing one of the test compounds in a predetermined concentration. The mixture was stirred thoroughly to prepare a test water. Ten female guppies (*Lebistes reticulatus*) of from 3 to 4 months of age were released into the test water which was maintained at 20° C. and the TLm (median tolerance limit, ppm) was determined. The results are set forth in Table 9.

TABLE 9

| Test compound | | TLm (48 hrs.) ppm |
|---|---|---|
| Compound (1) | cis-/trans- = 50:50 | >5 |
| Compound (2) | " | >10 |
| Compound (B) | " | <0.5 |
| Compound (C) | " | <0.5 |
| Compound (D) | " | <0.5 |
| Compound (E) | — | <0.5 |
| Compound (F) | cis-/trans- = 50:50 | <0.5 |
| Compound (G) | " | <1.0 |

TEST EXAMPLE-8

Fish toxicity test with carp (*Cyprinus carpio L*)

An acetone solution of one of the test compounds as mentioned in Table 10 and Tween-20 (the same surfactant as mentioned hereinbefore) was prepared. To 50 liters of water (30 cm deep) in a glass tank was added the above acetone solution. The mixture was stirred thoroughly to prepare an aqueous solution containing the test compound in a predetermined concentration. This was used as a test water. Five carps (*Cyprinus carpio L*) with a body weight of about 6 g and a body length of about 6 cm were released into each test water which was maintained at 21±1° C. After 48 hours, the test fish was examined for death. The TLm (median tolerance limit, ppm) was determined. The test water was moderately aerated. The results are set forth in Table 10.

Toxicity test with water-fleas (*Daphnia pulex*)

An acetone solution of one of the test compounds as mentioned in Table 10 and Tween-20 (the same surfactant as mentioned hereinbefore) was prepared. To 100 ml of water in a high-walled dish (9 cm in diameter, 7 cm deep) was added the above acetone solution. The mixture was stirred thoroughly to prepare an aqueous solution containing the test compound in a predetermined concentration. This was used as a test water. Twenty water-fleas (*Daphnia pulex*) were released into each test water which was maintained at 25±1° C. After 6 hours, the water-fleas were examined for deaths. The TLm (median tolerance limit, ppm) was determined. The results are set forth in Table 10.

TABLE 10

| Test compound | | TLm, ppm Carp (48 hrs.) | Water-flea (6 hrs.) | Ranking |
|---|---|---|---|---|
| Compound (1) | cis-/trans- = 20:80 | 2.6 | >40 | B |
| | trans- | 4.5 | >40 | B |
| Compound (2) | cis- | 0.83 | >40 | B |
| | cis-/trans- = 50:50 | 2.8 | >40 | B |
| | cis-/trans- = 30:70 | 4.9 | >40 | B |
| | cis-/trans- = 10:90 | 7.2 | >40 | B |
| | trans- | >10 | >40 | A |
| Compound (B) | cis-/trans- = 50:50 | 0.015 | — | C |
| Compound (C) | " | 0.0045 | — | C |
| Compound (D) | " | 0.0051 | — | C |
| Compound (E) | — | 0.0032 | — | C |
| Compound (G) | cis- | 0.013 | 5.0 | C |
| | cis-/trans- = 50:50 | 0.040 | — | C |
| | trans- | 0.090 | 1.7 | C |
| Compound (H) | cis-/trans- = 50:50 | 0.063 | — | C |
| Compound (L) | — | 0.032 | — | C |

The above ranking with symbols A, B and C were determined according to Japanese regulations relative to application of agricultural chemicals, and these symbols are defined as follows:

A: TLm (48 hrs.) value >10 ppm for carp and TLm (3 hrs.) value >0.5 ppm for water flea, wherein toxicity to fishes is not observed by usual application.

B: TLm (48 hrs.) value 10-0.5 ppm for carp; or TLm (48 hrs.) value >10 ppm for carp and TLm (3 hrs.) value <0.5 ppm for water flea, wherein appreciable toxicity to fishes is not observed by usual application but may be observed when applied to wide area at one time.

C: TLm (48 hrs.) value <0.5 ppm for carp, wherein toxicity to fishes is so strongly observed by usual application that both the application method and application area are strictly restricted.

rice leafhoppers (μg/g)] of the compounds (1) and (2) according to this invention, the control compounds (A) and (B), carbamate pesticide, i.e. carbaryl and Bassa (o-sec-butylphenyl methylcarbamate), and organophosphorus pesticide, i.e. fenitrothion, diazinon and malathion. The results are set forth in Table 4.

TABLE 4

| Test compound | | LD$_{50}$, μg/g |
|---|---|---|
| Compound (1) | cis-/trans- = 50:50 | 1.32 |
| | cis-/trans- = 30:70 | 0.85 |
| | trans- | 0.68 |
| Compound (2) | cis- | 0.44 |
| | cis-/trans- = 50:50 | 0.44 |
| | cis-/trans- = 30:70 | 0.40 |
| | trans- | 0.45 |
| Compound (A) | cis-/trans- = 50:50 | 1.22 |
| Compound (B) | cis-/trans- = 50:50 | 1.25 |
| Carbaryl | | 29.5 |
| Bassa | | 93.8 |
| Fenitrothion | | 4050 |
| Diazinon | | 72.2 |
| Malathion | | 565 |

TEST EXAMPLE-3

Mortality test with rice stem borers (*Chilo suppressalis Walker*) by topical application method Each of the compounds according to this invention and the control compounds (Table 5) was accurately weighed and dissolved in acetone to prepare a solution of predetermined concentration. Using a microsyringe, 0.5 μl of the above solution was applied to the thoracic abdominal region of each final-instar larva of rice stem borer (*Chilo suppressalis Walker*). Thereafter, the test larvae were released on a filter paper imbibed with water in a dish 9 cm in diameter and kept at a temperature of 25° C. The test larvae were used in groups of 20 individuals each. After 24 hours the larvae were examined for deaths and the percent mortality was calculated. The results are tabulated in Table 5.

TABLE 5

| Test compound | | % Mortality | |
|---|---|---|---|
| | | 1.0 μg/ Larva | 10 μg/ Larva |
| Compound (1) | cis- | 100 | 100 |
| | trans- | 85 | 100 |
| | cis-/trans- = 50:50 | 100 | 100 |
| Compound (2) | cis- | 100 | 100 |
| | trans- | 100 | 100 |
| | cis-/trans- = 50:50 | 100 | 100 |
| Compound (A) | " | 45 | 100 |
| Compound (B) | " | 95 | 100 |
| Compound (C) | " | 95 | 100 |
| Compound (D) | " | 100 | 100 |
| Compound (E) | — | 100 | 100 |
| Compound (G) | cis- | 40 | 100 |
| | trans- | 85 | 100 |
| | cis-/trans- = 50:50 | 90 | 100 |
| Compound (H) | " | 90 | 100 |
| | | 15 | 90 |

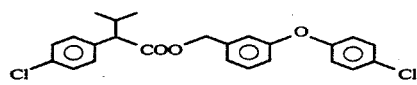

[hereinafter referred to as Compound (J)]

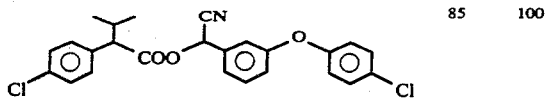

85 | 100

TABLE 5-continued

| Test compound | % Mortality | |
|---|---|---|
| | 1.0 μg/ Larva | 10 μg/ Larva |

[hereinafter referred to as Compound (L)]

TEST EXAMPLE-4

Mortality test with tobacco cutworms (*Prodenia litura Fabricius*) by topical application method Each of the compounds according to this invention and the control compounds (Table 6) was accurately weighed and dissolved in acetone to prepare a solution of predetermined concentration. Using a microsyringe, 0.5 μl of the above solution was dripped onto the thoracic adbominal region of each of 3-instar tobacco cutworm (*Prodenia litura Fabricius*) larvae. Thereafter, the larvae were released together with feed on a filter paper in a dish 9 cm in diameter and kept at a temperature of 25° C. The test larvae were used in groups of 20 individuals each. After 24 hours the insects were examined for deaths and the percent mortality was calculated. The results are shown in Table 6.

TABLE 6

| Test compound | | % Mortality 0.1 μg/Larva |
|---|---|---|
| Compound (1) | cis- | 100 |
| | trans- | 100 |
| | cis-/trans- = 50:50 | 100 |
| Compound (2) | cis- | 100 |
| | trans- | 100 |
| | cis-/trans- = 50:50 | 100 |
| Compound (A) | " | 35 |
| Compound (B) | " | 85 |
| Compound (G) | " | 65 |
| Compound (H) | " | 60 |
| Compound (J) | — | 0 |
| Compound (K) | — | 0 |
| Compound (L) | — | 35 |

TEST EXAMPLE-5

Mortality test with two-spotted spider mites (*Tetranychus urticae Koch*) by spray application method To a 5% aqueous solution of acetone was added dropwise a small amount of Tween-20 (polyethylene sorbitan monolaurate) as a surfactant. Then, each of the compounds according to this invention and the control compounds (Table 7) was accurately weighed and dissolved in the above 5% acetone-water solution to prepare a solution of 200 ppm. From 30 to 50 adult two-spotted spider mites (*Tetranychus urticae Koch*) were released on the leaves of kidney-bean plants in the dicotyledonous stage in a pot 9 cm in diameter, followed by a spray application of the above solution. The pot was kept in a constant-temperature chamber at 26° C. and two days later the mites were examined for deaths. The percent decrease of population was then calculated. The test compounds and results are shown in Table 7.

TABLE 7

| Test compound | | Percent decrease of population (%) |
|---|---|---|
| Compound (1) | cis- | 100 |
| | trans- | 100 |
| | cis-/trans- = 50:50 | 100 |
| Compound (2) | cis- | 100 |

TEST EXAMPLE-9

Acute toxicity test in rat by the oral route

Male rat weighting 260 to 270 g were orally dosed with each test compound as dissolved in olive oil (0.5 ml/100 g body weight) and the median lethal dose [$LD_{50}$: the amount of each test compound which killed 50% of dosed rats (mg/kg)] after 7 days was determined. The results are set forth in Table 11.

TABLE 11

| Test compound | | $LD_{50}$ mg/kg |
| --- | --- | --- |
| Compound (1) | cis-/trans- = 50:50 | >3000 |
| Compound (2) | " | >3000 |
| Compound (B) | " | 300 |
| Compound (C) | " | 310 |
| Compound (E) | — | 440 |

FORMULATION EXAMPLE-1

Thirty (30) parts each of the cis- and trans-isomers and a 50:50 mixture of the cis- and trans-isomers of Compound (1) and of Compound (2) were prepared. To each of them were added 50 parts of xylol and 20 parts of Sorpol SM-200 (the same surfactant as mentioned hereinbefore). Each mixture was stirred well to prepare 30% emulsifiable concentrates of the respective active compounds.

FORMULATION EXAMPLE-2

One (1) part each of the cis- and trans-isomers and a 50:50 mixture of the cis- and trans-isomers of Compound (1) and of Compound (2) was prepared. To each of them were added 3 parts of dimethylformamide and 1 part of Tween-20 (the same surfactant as mentioned herinbefore) followed by thorough mixing. Each mixture was diluted with water with stirring to make 100 parts of a 1% emulsifiable concentrate of the corresponding compound.

FORMULATION EXAMPLE-3

Two -tenths (0.2) parts each of the cis- and trans-isomers and a 50:50 mixture of the cis- and trans-isomers of Compound (1) and of Compound (2) were respectively dissolved in 20 parts of acetone, followed by addition of 99.8 parts of clay. After thorough stirring, the acetone was evaporated from each mixture and the residue was further stirred well in a triturator to prepare a 0.2% dust of the corresponding compound.

FORMULATION EXAMPLE-4

Five-tenths (0.5) parts each of the cis- and trans-isomers and a 50:50 mixture of the cis- and trans-isomers of Compound (1) and of Compound (2) were respectively dissolved in 20 parts of acetone, followed by addition of 99.5 parts of clay. After thorough stirring, the acetone was evaporated from each mixture and the residue was further stirred well in a triturator to prepare a 0.5% dust of the corresponding compound.

FORMULATION EXAMPLE-5

Two-tengths (0.2) parts each of the cis- and trans-isomers and a 50:50 mixture of the cis- and trans-isomers of Compound (1) and of Compound (2) was dissolved in kerosene with stirring to make 100 parts. The above procedure yielded oil preparations of the respective active compounds.

FORMULATION EXAMPLE-6

To 20 parts each of the cis- and trans-isomers and a 50:50 mixture of the cis- and trans-isomers of Compound (1) and of Compound (2) was added 5 parts of Sorpol SM-200 (the same surfactant as mentioned hereinbefore). After thorough mixing, 75 parts of clay was added to each mixture and stirred well in a triturator. The above procedure yielded wettable powders of the respective active compounds.

UTILITY EXAMPLE-1

A 1% emulsifiable concentrate of each test compound as prepared by the procedure described in Formulation Example 2 was diluted with water to prepare a test solution of predetermined concentration.

Rice plants, 4 weeks after sowing (cultivated in a pot 6 cm in diameter, 7 seedlings) were dipped in the above solution and after allowing them to dry in the air, the pot was covered with a wire-mesh cage. Then, 30 adult brown planthoppers (*Nilaparvata lugens Stal*) were released into the cage and the pot was kept in a constant-temperature chamber at 25° C. After 24 hours the insects were examined for deaths and the median lethal concentration [$LC_{50}$; the concentration (ppm) of each test compound which kills 50% of the test insects in 24 hours] was determined. The results are set forth in Table 12.

To further confirm the low toxicity to fish and high pesticidal activity of Compounds (1) and (2) according to this invention as evidenced by the fish toxicity tests with carps and the above tests, fish toxicity safety factors were calculated from the fish toxicity and pesticidal test data. These fish toxicity safety factors are indicators of safety to fish inhabiting a paddy field to which Compounds (1) and (2) may be actually applied for pest control purposes.

It is first assumed that such a pesticidal solution would normally be applied at the rate of 100 l per 10 ares of paddy field. It is also assumed that a solution (100 l) corresponding to the $LC_{50}$ of the compounds would be applied to 10 ares of a paddy field carrying a cover water with a depth of 5 cm above ground surface and that all the solution would then find its way into the cover water. The expected maximum concentration of the compound in the cover water is then calculated. The fish toxicity safety factor of a pesticidal compound is defined as the value obtained by dividing the TLm (ppm) of the particular compound by the maximum concentration of the compound in cover water. The meaning of the value of the fish toxicity safety factor being one (1) is that the maximum concentration of the particular compound in cover water corresponds to the TLm of said compound. It is understood that when the pesticidal compound having a fish toxicity safety factor value of less than one (1) is applied to a paddy field, it has a risk of destroying the fish inhabiting there, and that the higher the safety factor value, the higher is the safety of the compound to fish.

This fish toxicity safety factor will now be explained in further detailed by taking the trans-isomer of Compound (2) of this invention as an example.

The quantity of water required to form a 5 cm-deep cover water over 10 ares of paddy field is 50 tons and if 100 liters of a solution corresponding to the $LC_{50}$ of the trans-isomer of Compound (2) is applied to the above cover water, the maximum concentration of the trans-isomer in the water will be 0.36 ppm. On the other hand, the toxicity to fish of this compound is TLm >10 ppm. Therefore, by dividing the TLm (i.e. >10 ppm) by the above cover water maximum concentration (i.e. 0.36 ppm), we obtain a fish toxicity safety factor of >28. Thus, the concentration of the trans-isomer of Compound (2) which kills 50% of pests corresponds to less than 1/28 of the concentration of the same isomer which kills 50% of fish. In other words, this means that the trans-isomer of Compound (2) is extremely safe to fish.

TABLE 12

| Test compound | | Toxicity to fish TLm (ppm) | Pesticidal activity LC$_{50}$ (ppm) | Fish toxicity safety factor |
|---|---|---|---|---|
| Compound (1) | cis-/trans- = 20:80 | 2.6 | 520 | 2.5 |
| | trans- | 4.5 | 650 | 3.5 |
| Compound (2) | cis- | 0.83 | 200 | 2.1 |
| | cis-/trans- = 50:50 | 2.8 | 190 | 7.4 |
| | cis-/trans- = 30:70 | 4.9 | 180 | 13.6 |
| | cis-/trans- = 10:90 | 7.2 | 180 | 20 |
| | trans- | >10 | 180 | >28 |
| Compound (B) | cis-/trans- = 50:50 | 0.015 | 700 | 0.01 |
| Compound (C) | " | 0.0045 | 210 | 0.01 |
| Compound (G) | cis- | 0.013 | 620 | 0.01 |
| | cis-/trans- = 50:50 | 0.04 | 450 | 0.04 |
| | trans- | 0.09 | 380 | 0.12 |
| Compound (E) | — | 0.0032 | 1550 | 0.001 |
| Compound (L) | — | 0.032 | 2260 | 0.0071 |

UTILITY EXAMPLE-2

A 30% emulsifiable concentrate of each of the cis- and trans-isomers and a 50:50 mixture of the cis- and trans-isomers of Compound (1) and Compound (2) as prepared by the procedure described in Formulation Example-1 was diluted with water to a concentration of 80 ppm as active compound. Rice plants 4 weeks after sowing in pots (each pot 6 cm in diameter, 7 seedlings) were sprayed with the above solution at the rate of 7 ml/pot and, after drying in the air, each pot was covered with a wire-mesh cage. Then, 20 female adult green rice leafhoppers (*Nephotettix cincticeps Uhler*) were released into the cage. The caged pots were kept in a constant-temperature chamber at 25° C. After 24 hours, the test insects were examined for deaths and the percent mortality was determined. In all groups, the mortality values were not less than 90%.

UTILITY EXAMPLE-3

A 30% emulsifiable concentrate of each of the cis- and trans-isomers and a 50:50 mixture of the cis- and trans-isomers of Compound (1) and of Compound (2) as prepared by the procedure described in Formulation Example-1 was diluted with water to a concentration of 80 ppm as active compound. Rice plants 4 weeks after sowing in pots (each pot 6 cm in diameter, 7 seedlings) were sprayed with the above diluted solution at the rate of 7 ml/pot and, after drying in the air, each pot was covered with a wire-mesh cage. Then, 30 adult small brown planthoppers (*Laodelphax striatellus Fallén*) were released into the cage. The pots were kept in a constant-temperature chamber at 25° C. After 24 hours the test insects were examined for deaths and the percent mortality was calculated. In all groups, the mortality was not less than 90%.

UTILITY EXAMPLE-4

A 0.2% dust preparation of each of the cis- and trans-isomers and a 50:50 mixture of the cis- and trans-isomers of Compound (1) and of Compound (2) as prepared by the procedure described in Formulation Example-3 was applied to rice seedlings by means of a bell-jar duster at the rate of 5 kg per 10 ares. Then, 30 green rice leafhoppers (*Nephotettix cincticeps Uhler*) resistant to organophosphorus and carbamate pesticides were released. After 24 hours the insects in each group were examined for deaths and the percent mortality was calculated. In all cases, the mortality was not less than 90%.

UTILITY EXAMPLE-5

An acetone solution of one of the test compounds as mentioned in Table 13 and Tween-20 (the same surfactant as mentioned hereinbefore) was prepared. This acetone solution was diluted with water to prepare a solution containing the test compound in a predetermined concentration. Leaves of soy bean in pots were sprayed with the above diluted solution at the rate of 20 ml/pot and, after one day, ten 3-instar larvae of tobacco cutworm (*Prodenia litura*) were released on the leaves. The pots were kept in a constant-temperature chamber at 25° C. After 2 days, the test larvae were examined for deaths and the percent mortality was calculated. The results are set forth in Table 13.

TABLE 13

| Test compound | | % Mortality | |
|---|---|---|---|
| | | 6.5 ppm | 13 ppm |
| Compound (1) | cis-/trans- = 50:50 | 90 | 100 |
| Compound (2) | " | 100 | 100 |
| Compound (B) | " | 60 | 90 |
| Compound (H) | " | 40 | 100 |

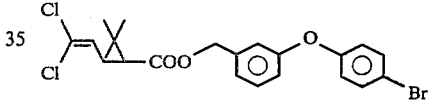

10 / 100

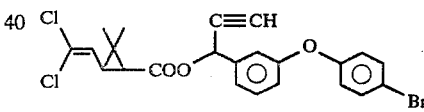

0 / 90

UTILITY EXAMPLE-6

A 0.5% dust preparation of each of the cis- and trans-isomers and a 50:50 mixture of the cis- and trans-isomers of Compound (1) and of Compound (2) as prepared by the procedure described in Formulation Example-4 was applied to rice seedlings by means of a bell-jar duster at the rate of 1 kg per 10 ares. Then, 30 green rice leafhoppers (*Nephotettix cincticeps*) resistant to organophosphorus and carbamate pesticides were released. After 24 hours, the insects in each group were examined for deaths and the percent mortality was calculated. In all cases, the mortality was not less than 90%.

UTILITY EXAMPLE-7

A 0.5% dust preparation of each of the cis- and trans-isomers and a 50:50 mixture of the cis- and trans-isomers of Compound (1) and of Compound (2) as prepared by the procedure described in Formulation Example-4 was applied to rice seedlings, on which 30 adult brown planthoppers (*Nilaparvata lugens*) were released, by means of a bell-jar duster at the rate of 1 kg per 10 ares. After 24 hours, the insects in each group were examined for deaths and the percent mortality was calculated. In all cases, the mortality was not less than 90%.

UTILITY EXAMPLE-8

Phytotoxicity test

A 2,000 ppm solution of each of the cis- and trans-isomers and a 50:50 mixture of cis- and trans-isomers of Compound (1) and of Compound (2), and a 50:50 mixture of the cis- and trans-isomers of Compound (B) and Compound (E) was applied to the leaves of the following crop plants.

Test crop plant:

| Name | Leaf stage |
| --- | --- |
| Chinese cabbage | 4th–5th leaf stage |
| Radish | 2nd–3rd leaf stage |
| Tomato | 3.5th–4.5th leaf stage |
| Cucumber | 2nd–2.5nd leaf stage |
| Eggplant | 2.5nd–3.5th leaf stage |
| Beat | 2nd–3rd leaf stage |
| Soy bean | 1st dicotyledonous stage |

After 10 days, the crop plants were examined for their phytotoxicities. Compounds (1), (2) and (B) each did not cause any injury to each one of the crop plants. But, Compound (E) caused chlorosis to each one of the crop plants and did large damage to the same.

What is claimed as new and intended to be covered by Letters Patent of the United States is:

1. A method for controlling insects or acarids which comprises applying to a habitat of the insects or acarids an effective amount of a substituted cyclopropanecarboxylic acid ester of the general formula:

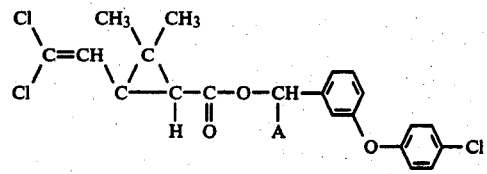

wherein A is a hydrogen atom or an ethynyl group and said ester is applied to rice paddy.

* * * * *